United States Patent [19]

Redenbaugh

[11] Patent Number: 4,562,663

[45] Date of Patent: Jan. 7, 1986

[54] ANALOGS OF BOTANIC SEED

[75] Inventor: M. Keith Redenbaugh, Davis, Calif.

[73] Assignee: Plant Genetics, Inc., Davis, Calif.

[21] Appl. No.: 433,688

[22] Filed: Oct. 12, 1982

[51] Int. Cl.$^4$ .......................... A01C 1/06; A01G 9/10
[52] U.S. Cl. ......................................... 47/58; 47/57.6
[58] Field of Search ................................ 47/58, 57.6; 111/DIG. 1; 435/177–180

[56] References Cited

U.S. PATENT DOCUMENTS

| | | | |
|---|---|---|---|
| 3,545,129 | 12/1970 | Schreiber et al. | 47/57.6 |
| 3,698,133 | 10/1972 | Schreiber | 47/57.6 |
| 3,973,355 | 8/1976 | McKenzie | 47/57.6 X |
| 4,241,537 | 12/1980 | Wood | 47/57.6 X |
| 4,245,432 | 1/1981 | Dannelly | 47/57.6 |
| 4,249,343 | 2/1981 | Dannelly | 47/57.6 |
| 4,352,883 | 10/1982 | Lim | 435/178 |

OTHER PUBLICATIONS

Berdahl, J. D. et al., "Germination and Emergence of Russian Wildrye Seeds Coated with Hydrophilic Materials"—Agron. J. 72: 1006–1008.
Dexter, S. T. et al., "Acceleration of Water Uptake and Germination of Sugarbeet Seedballs by Surface Coatings of Hydrophilic Colloids"—Agron. J. 51: 388–89.
Kitto, S. L. et al., Abstracts in Hort. Sci., 15: 439 (1980), 16: 452 (1981), 17: 488 (1982) and 18: 618 (1983).
Chrimes, J. R. et al., Sci. Hort. 17: 15 (1982).
Darby, R. J., Expl. Agric. 16: 153 (1980).
Gray, D., Ann. Appl. Biol. 88: 185 (1978).
Gray, D., J. Royal Hort. Soc. 104, Part 5: 204 (1979).
Gray, D., Hort. Reviews 3: 1 (1981).
Hardaker, J. et al., Expl. Agric. 14: 17 (1978).
Longden, P. L. et al., Agric. Sci. 93: 541 (1979).
R. W. Allard, "Principles of Plant Breeding", (John Wiley and Sons, Inc. 1960), title page and table of contents.
W. C. Anderson and J. B. Carstens, J. Amer. Soc. Hort. Sci., 102 (1), pp. 69–73 (1977).
D. Gray, J. Hort. Sci. 53: 23–30 (1978).
D. A. Evans and W. R. Sharp, in "Application of Plant Cell and Tissue Culture to Agriculture and Industry", D. T. Tomes et al., eds. pp. 212–214 (1982).
K. A. Walker and S. J. Sato, Plant Cell Tiss. Org. Cult. 1: 109–121 (1981).
H. E. Street, ed., "Plant Tissue and Cell Culture", Univ. of California Press (1977), title page and table of contents.
T. Murashige, Ann. Rev. Plant Physiol. 25: 135–166 (1974).
M. Monnier, in "Frontiers of Plant Tissue Culture 1978", T. A. Thorpe, ed., (The International Association for Plant Tissue Culture, Univ. of Calgary, Alberta, pp. 277–280, 1978).
Shenk, R. and A. Hildebrandt, Can. J. Bot. 50: 199–204 (1972).
K. A. Walker et al., Am. J. Bot. 65: 654–659 (1978).
K. A. Walker, et al., Plant Sci. Lett. 16: 23–30 (1979).
Murashige, T. and F. Skoog, Phsiol. Plant. 15: 473–497 (1962).

Primary Examiner—Robert E. Bagwill
Attorney, Agent, or Firm—Limbach, Limbach & Sutton

[57] ABSTRACT

A novel analog to natural botanic seed, together with a process for producing this analog are provided. Plant meristematic tissue capable of producing an entire plant body, and generally from somatic sources, is encapsulated in a gel which protects the tissue during development, while allowing the meristem to grow and mature as normal plants. The chemical and mechanical characteristics of the gel can be varied to suit any plant or method of handling, while allowing inclusion of growth and development enhancing substances.

19 Claims, No Drawings

ANALOGS OF BOTANIC SEED

BACKGROUND OF THE INVENTION

This invention relates to production of analogs of botanic seed wherein the genotype may be identical to the parental strain.

The conventional techniques of crop improvement in agriculture involve a search for strains of plants which exhibit new and useful characteristics, or refine and improve on existing ones. The search has evolved from mere selection of a desirable parent plant to hybridization between parental strains which each exhibit desirable characteristics to, finally, crossbreeding between homozygous strains such that identical $F_1$ progeny will be produced in each subsequent crossbreeding.

The conventional methods of maintaining genetic identity are well known and described in the literature. See, e.g. R. W. Allard "Principles of Plant Breeding," (John Wiley and Sons, Inc., 1960). The maintenance of purebred strains and the repeated crossbreeding to obtain $F_1$ progeny are time consuming and labor intensive.

An additional limitation on the sexual reproduction of parental strains has been the low seed productivity per plant. This often results from low vigour which is manifested by heavily inbred strains. Finally, only a relatively limited number of purebred lines may be produced, and this results in a decreased pool of genetic characteristics available for selection.

It has been recognized that some of these difficulties may be overcome by vegetative propagation of the parental strain. See: W. C. Anderson and J. B. Carstens, "Tissue Culture Propagation of Broccoli, *Brassica oleracea* (Italica Group), for use in $F_1$ Hybrid Seed Production," J. Amer. Soc. Hort. Sci., 102(1), pp. 69–73 (1977). This technique avoids the problem of the change in parental strain genetic characteristics through sexual reproduction. However, the sexual cross to produce $F_1$ seed does not guarantee uniform progeny where there is chromosomal trait segregation in the parental strains.

It has been suggested that a desirable species may be propagated vegetatively, and the somatic embryos or rooted plantlets produced thereby transferred to the field. However, this technique involves skilled labor in tissue culture laboratories, a transfer to a hot-house or nursery, and upon attaining sufficient acclimatization, a transplantation to the field. This procedure is costly and time consuming in comparison with the traditional methods of seeding.

To overcome some of these difficulties, the technique of fluid drilling has been developed. Fluid drilling methods have been used with pregerminated seed, e.g., D. Gray, "Comparison of Fluid Drilling and Conventional Establishment Techniques on Seedling Emergence and Crop Uniformity in Lettuce," J. Hort. Science. 53:23–30 (1978), and it has been suggested that fluid drilling may be adaptable to transfer somatic embryos directly to the field. D. A. Evans and W. R. Sharp, "Application of Tissue Culture Technology in the Agricultural Industry," in Application of Plant Cell and Tissue Culture to Agriculture and Industry, D. T. Tomes et al., eds. (University of Guelph Press, pp. 212–13, 1982). However, fluid drilling technology is capital intensive and requires the purchase of machinery and the development of new techniques in the agricultural community, which has been historically resistant to such change.

Thus, an object of this invention is to provide a technique whereby cultured plant tissue may be insulated from harmful conditions.

Another object of this invention is to decrease the time for raising a mature or vigorous seedling from meristematic tissue, somatic embryos or tissue-cultured plants.

Yet another object of the invention is to provide a medium to deliver the cultured plant tissue together with adjunctives facilitating seedling stand establishment.

A further object of the invention is to reduce the amount of handling between the development of the cultured plant tissue and its planting in the field.

A still further object of the invention is to reduce the need for special handling techniques and special technology during the development and growth of cultured plant tissue and, thus, overcome resistence to the introduction of new technology by adapting to existing methods of seed planting technology.

A final object of the invention is to provide a large scale, economical method to clone superior plants or hybrid plants.

DISCLOSURE OF INVENTION

Briefly, in accordance with the invention, analogs of botanic seed are created by encapsulating totipotent meristematic tissue in a gel which permits germination and development.

The invention is based in part on the recognition that botanic seed contains meristematic tissue which has the potential to differentiate to produce an entire plant body. Included also are various accessory structures which promote the development and survival of the plant.

The invention also includes a recognition that totipotent meristematic tissue may be isolated from many sources and the accessory structures may be selectively included, or improved upon, in encapsulated meristematic tissue.

Further, many of the advantageous properties of the seed coat and accessory structures may be recreated by the gel used to encapsulate the meristematic tissue. The gel can cushion the meristem from mechanical stress. The gel can accept and hold various adjunctives which provide nutrition or enhance development. The gel can allow germination inhibitors to diffuse away at a controlled rate, thus allowing preselected germination time. The outer surface of the gel can be treated to harden it or alter its permeability.

In accordance with one aspect of the invention, meristematic tissue is isolated by inducing the formation of somatic embryos. These embryos are then encapsulated in a gel which permits development.

In accordance with another aspect of the invention, meristematic tissue is isolated from somatic sources and, having the potential to differentiate to produce an entire plant body, is encapsulated without somatic embryogenesis being induced.

In accordance with another aspect of the invention, meristematic tissue is isolated from zygotic or germ line sources, and encapsulated in a gel which will permit development.

The invention is particularly advantageous in creating analogs to botanic seed which promote the delivery of superior clones or hybrids to the field using traditional planting methods.

BEST MODE FOR CARRYING OUT THE INVENTION

Selection of Meristematic Tissue

Botanic seed is a means which has evolved to deliver the progeny of plants to sites which are suitable for development and growth. The essential element of botanic seed is the meristematic tissue which differentiates to form an entire plant body. Also included are various other accessory structures which provide nutrition or protection to the developing embryo.

Cultured plant tissue may be derived from numerous sources, including somatic tissue, zygotic tissue or germ line tissue. Regardless of its source, the tissue must pass through a meristem stage in order to undergo organogenesis and develop into a regenerated plant body.

Plant meristematic tissues are units of organization. Some meristematic tissues have the capacity to produce an entire plant body; others produce only selected tissues. Those which produce an entire plant body are termed totipotent.

It is an inherent property of an embryo to recapitulate ontogeny. This capacity resides in the meristem, and the other structures in a seed or embryo are accessory to this meristematic tissue.

Those tissue sources which are not ordinarily involved in reproduction may, under appropriate circumstances or inducement, form meristematic tissue.

As a first step in the production of encapsulated somatic embryos, crop strains must be selected which are capable of somatic embryogenesis. For a representative list of such species see D. A. Evans and D. R. Sharp, "Application of Tissue Culture Technology in the Agricultural Industry," in Application of Plant Cell and Tissue Culture to Agriculture and Industry, D. T. Tomes et al., editors, (University of Guelph Press, page 214, 1982), which is incorporated herein by reference. Further species may be shown capable of somatic embryogenesis with further experimentation and refinement of technique.

Once the appropriate strain is selected, preparation of somatic embryos may proceed by any of numerous known techniques. For example, in alfalfa, see K. A. Walker and S. J. Sato, "Morphogenesis in Callus Tissue of *Medicago Sativa*: The Role of Ammonium Ion in Somatic Embryogenesis," Plant Cell Tiss. Org. Cult. 1:109–121 (1981), which is incorporated herein by reference. For other techniques known to the art see "Plant Tissue and Cell Culture", H. E. Street, ed., Univ. of Calif. Press (1977).

The somatic tissue of certain other species are able to undergo shoot organogenesis without the intermediate formation of somatic embryos. See, T. Murashige, "Plant Propagation Through Tissue Culture, Ann. Rev. Plant Physiol. 25:135–46 (1974). Tissue from these plants may be encapsulated without the preliminary embryogenesis step, and mature plants grown therefrom.

As an alternative, zygotic embryos may be used when for example the species is incapable of somatic embryogenesis. These zygotic embryos may be grown in culture or suspension, and then may be encapsulated with or without their seed coat and other accessory structures.

In certain wide crosses, a fertile embryo is formed but the endosperm fails to develop and the embryo then dies. Thus the cross appears sterile, but viable progeny can be obtained by isolating the embryo from the aborted ovuli. The zygotic embryos may be separated from their seed coat and then encapsulated with additives which will enhance their growth and viability. See for example M. Monnier, "Culture of Zygotic Embryos," Frontiers of Plant Tissue Culture, T. A. Thorpe, ed. (The International Association for Plant Tissue Culture, University of Calgary, Alberta, Canada pp. 277–80, 1978).

Encapsulation Media

It has been recognized that the germination and development of seeds may be enhanced by coating them with various materials. For example, it has been reported that coating seeds with Super Slurper (trade name) will result in a water-absorbent reservoir which improves the germination rate in arid conditions.

It has also been suggested that encapsulation of somatic embryos may be accomplished.

It has also been demonstrated that perishable foods may be preserved by coating them with a complexed carbohydrate, e.g. Earle U.S. Pat. No. 3,395,024.

The meristematic tissue may be enclosed in any of numerous media which provide an appropriate encapsulation matrix, hereafter termed "gel". In general, a gel must allow meristem or embryo respiration by permitting diffusion of gases. The gel should provide an environment strong enough to resist external abrasion and adverse forces, yet pliable enough to allow the growth of the embryo and its germination at the appropriate time. It may be desirable to use various gels in combination, either as a mixture or in layers, to achieve the desired results.

Gels which have been found useful for encapsulating meristematic tissue include sodium alginate, guar gum, carrageenan with locust bean gum, and sodium alginate with gelatin. Other suitable gels include, but are not limited to:

TABLE 1

| Gel Agents |
|---|
| I. Natural Polymers |
|    A. Ionic bonds (requires complexing agents) |
|       Furcellaran |
|       Pectin |
|       Hypnean |
|       Dextran |
|       Tamarind |
|       Guar Gum |
|    B. Hydrophobic Interactions |
|       Amylose |
|       Agar |
|       Agarose |
|       Agar with Gelatin |
|       Gelatin |
|       Starch |
|       Amylopectin |
|       Cornhull Gum |
|       Starch Arabogalactan |
|       Gum Ghatti |
|       Gum Karagan |
|       Ti Gum |
|       Gum Tragacanth |
|       Wheat Gum |
|       Chitin |
|       Dextrin |
| II. Chemically Modified Natural Polymers |
|    A. Ionic bonds (requires a complexing agent) |
|       Ethyl Succinylated Cellulose |
|       Succinylated Zein |
|    B. Hydrophobic Interactions |
|       Methylcellulose |
|       Hydroxyethyl Cellulose |
|    C. Covalent Bonds |

TABLE 1-continued

Gel Agents

Gelatin with Glutaraldehyde

III. Synthetic Polymers
   A. Covalent Bonds
      Polyacrylamide
   B. Hydrophobic Interactions
      Polyethylene Glycol
      Polyvinylpyrrolidone
      Polyoxyethylene
      Hydrophilic Urethane
      Polyvinylacetate
      Vinyl Resins
      Hydron (hydroxyethylmethacrylate)
      2-methyl-5-vinylpyridine-methylacrylate-methacrylic acid
   C. Ionic Bonds
      sodium poly(styrene sulfonate) with poly(vinyl methyl pyridinium) chloride
      sodium poly(styrene sulfonate) with poly(vinyl benzyl trimethyl ammonium) chloride
      strongly acidic polyanion with strongly basic polycation IV. Stabilizing Compounds
   1. Trade Names
      Super Slurper
      Viterra
      Laponite
      Gelrite
      SeaKem
      SeaPlaque
      SeaPrep
      IsoGel
   2. Organic Compounds
      Methylan Clear Wallpaper Paste
      Lactose
      Wax
      Protein Colloids
   3. Inorganic Compounds
      a. Clay
      b. Compounds that adhere by means of a water-soluble plastic such as methylcel:
         Fly Ash
         Feldspar
         Celrite
         Bentonite
         Vermiculite
         Diatomacous Earth
         Lime
         Calcium Carbonate

Selecting Optimum Gels

A gel chosen for encapsulation would ideally include the following characteristics (although the invention may be practiced in other modes):

1. A compliance adequate to protect and cushion the meristem;
2. The interior material would have solubility characteristics such that it can accept and contain adjunctives, including but not limited to aqueous or hydrophobic substances;
3. An outer surface to provide a protective barrier to mechanical stress, facilitate handling and maintain meristem viability;
4. Sufficient gel strength to maintain capsule integrity, but still allow the meristem to break out during germination.

Encapsulation with Selected Gel

Once the gel has been chosen, there are numerous parameters which influence the characteristics previously mentioned.

A sodium alginate solution, for example, will form a gel when a complexing agent is added. Calcium chloride ($CaCl_2$) is generally used, however, lanthanum chloride, ferric chloride, cobaltous chloride, calcium nitrate and calcium hydroxide are also acceptable, as are other compounds generally with multivalant cations.

A chosen gel will have a range of concentrations usable in working the invention. A concentration should be chosen to optimize ease of handling, gelling time, strength of gel and coating thickness around the meristematic tissue. If the gel is too dilute, the tissue may settle during gel formation and produce an uneven encapsulation.

The sodium alginate may be prepared in a concentration of 1 to 10% w(in grams)/v(in milliliters) in water, more usually 2 to 10% and ideally from 3 to 5%.

The meristematic tissue to be encapsulated may then be added to the sodium alginate solution at a concentration of 1 to 50 meristems per milliliter, more usually from 5 to 20 meristems per milliliter. This concentration will vary as the appropriate size of meristematic tissue varies with species, source and stage of development.

The dispersed meristematic tissue in gel solution may then be added dropwise to the complexing agent. Alternatively, the gel solution and complexing agent may be mixed by any of numerous techniques known to the art. These may include droplet formation and agent addition as a one step process by a vibrating nozzle which ejects a gel droplet from one source and coats the droplet with complexing agent from another.

The calcium chloride (or other complexing agent) may be made up in solution at a concentration of 1 to 1,000 millimolar, more usually 20 to 500 millimolar and ideally from 50 to 100 millimolar. Other complexing agents will have different preferred concentration ranges.

The time for gel formation and the temperature of the gelling solutions are interrelated parameters, for selected concentrations of gel and complexing agent. The temperature should be chosen so as to avoid damage to the meristematic tissue, usually in the range of 1° to 50° C., more usually 10° to 40° C., and preferably at 20° to 40° C.

Within the range of acceptable temperatures, a particular value may be chosen to give the shortest possible gelling time consistent with complete gel formation. Typically, the gel will form immediately, but the complexation takes much longer. For a solution of sodium alginate at a concentration of 3.2 grams per 100 milliliters $H_2O$, calcium chloride solution concentration of 50 millimolar and 25° C. reaction temperature, adequate gelling is obtained in 5 to 120 minutes, more often 10 to 90 minutes and is usually sufficiently complete in 30 to 60 minutes.

The gel characteristics described above are modifiable for each gel, but are determined generally by the concentration parameters and chemical properties of the gel.

Hardening Capsules

Subsequent to encapsulation, it may be desirable to increase the rigidity of the outer surface of the gel matrix, through numerous techniques known to the art. In this manner, a softer gel may be used for the encapsulation and inclusion of appropriate additives, and in the outer surface resistance to abrasion and penetration may be increased with no loss of meristem viability.

The encapsulated meristematic tissue may be subjected to a partial desiccation, which results in a more rigid outer surface.

Alternatively, the encapsulated meristematic tissue formed of a selected gel may again be coated with a thin layer of a more rigid gel, or may be encased in a gelatin capsule available through commercial sources.

The surface may also be hardened by treatment with various chemical agents known to the art, which increase the gel surface breaking resistance.

Such techniques include, in part:

TABLE 2

| | Capsule Coating Compounds |
|---|---|
| I. | Coacervation |
| | Gelatin and Gum Arabic |
| | Lecithin and Cephalin with Cellulose Nitrate |
| | Paraffin Oil with Cellulose Nitrate |
| II. | Interfacial Polymerization |
| | Sebacoyl Chloride with Hexanediamine |
| III. | Tannic Acids |
| | Persimmon Tannin |
| | Chinese Gallotannin |
| IV. | Poly Amino Acids |
| | Polyornithine |
| | Polylysine |
| | Polycitrulline |
| | Polyarginine |
| | Polyhistidine |
| | Polyasparagine |
| | Polyglutamine |
| | Combination of Poly-L-Amino acids |
| V. | Glutaraldehyde |
| | Glutaraldehyde with gelatin |
| VI. | Gelatin capsules |

In utilizing the means of hardening the outer surface of the gel capsule, care must be taken to avoid damage to the meristematic tissue. For example, crosslinking the gel matrix with glutaraldehyde will provide surface strength, but if the glutaraldehyde is applied for an extended period of time, it will penetrate the gel completely and damage the meristematic tissue. This time period will vary with the gel material, the thickness of the gel coat and the temperature of the solutions.

It has been noted that certain of the above-mentioned treatments, e.g. polylysine, will change the water retention characteristics of the gel, but not the breaking strength. Thus by appropriate combination of treatments, most gel characteristics may be adjusted to their desired values.

Further Modifications

In agricultural applications, it is generally preferred that harvesting be accomplished in a brief period of time and in the appropriate season. Therefore, either before or during the gelling process, it may be desirable to synchronize the germination of the meristems or embryos through techniques known to the art, such as the use of mitotic blockers or sizing through sieves, so that any given batch of encapsulated meristems or somatic embryos will germinate at approximately the same time.

While the gel solution is being prepared, it may be desirable and appropriate to include certain adjunctives which will not interfere with the gel formation, but which may provide germination control, nutrition, disease resistance, pest resistance, nitrogen fixation capability, herbicide capability, or compounds which enhance embryogenesis or organogenesis. For example, abscisic acid, or high concentrations of sucrose, will inhibit germination. These adjunctives may be encapsulated with the meristematic tissue, and germination will occur only when the adjunctive has been removed by diffusion or otherwise.

Subsequent to encapsulation, it may be desirable to store the encapsulated meristematic tissues, transport them to the field, hothouse, or the nursery, and treat them in a manner consistent with botanic seed.

Planting these encapsulated meristematic tissues may be accomplished in the nursery or hothouse for species unable to tolerate the ambient climatic conditions without some period of acclimatization. Alternatively, for more hardy species, the encapsulated meristems may be planted directly in the field through numerous techniques employed in the art for botanic seed.

Experimental

In order to demonstrate the invention, the following experiments were carried out with a variety of meristematic tissue material, and gel media. All quantities labeled percent (%) are grams per 100 milliliters, unless otherwise indicated.

EXAMPLE A (Alfalfa somatic embryo)

1. Encapsulation with sodium alginate

Callus from alfalfa, *Medicago sativa* L. strain RA-3, is induced to form somatic embryos by a 3–4 day exposure to Shenk and Hildebrandt (SH) medium (Can. J. Bot. 50:199–204, 1972), supplemented with 50 micromolar 2,4-dichlorophenoxyacetic acid (2,4-D) and 5 micromolar kinetin. The tissue is then transferred to a 2,4-D- and kinetin-free SH regeneration medium. This procedure is explained in detail in: K. A. Walker, et al. "The Hormonal Control of Organ Formation in Callus of *Medicago sativa* L. Cultured in Vitro," Am. J. Bot. 65:654–659 (1978); K. A. Walker, et al., "Organogenesis in Callus Tissue of *Medicago sativa*, The Temporal Separation of Induction Process from Differentiation Processes," Plant Sci. Lett. 16:23–30 (1979); and K. A. Walker and S. J. Sato (1981) as cited elsewhere herein. These articles are incorporated herein by reference.

Somatic embryos form over a period of one to three weeks. At this point, the cultured somatic embryos may be synchronized, or be encapsulated directly.

The somatic embryos were adjusted to a concentration of 10 embryos per milliliter of sterile 3.2% sodium alginate at 25° C. The mixture was stirred into a slurry and then dispensed dropwise from a 5 milliliter Pipettman pipette with sterile tip into 500 milliliters of 50 millimolar calcium chloride at 25° C. At these concentrations, capsules form immediately, but the complete complexation takes 30 to 60 minutes. At this point, the calcium chloride solution is poured off and the capsules are washed twice in SH liquid medium. Using this technique, 50% of the capsules contain embryos. The capsules were then cultured on SH medium in a room with 16 hours of light per day in order to promote germination.

Using the above protocol, germination rates of 56 to 70% were achieved. Subsequently, some of these plants were raised under greenhouse conditions.

1.a As an alternative complexing agent, 8 to 80 millimolar ferric chloride ($FeCl_3$) can replace calcium chloride in the protocol of A.1.

1.b As an alternative complexing agent 10 to 100 millimolar lanthanum chloride may replace calcium chloride in the protocol of A.1.

1.c As an alternative germination method, the encapsulated somatic embryos may be inserted directly into a plug of peat composition (an Isocyanate and polyalcohol pre-polymer combined with water and peat. Available from Castle & Cook Techniculture, Inc.).

2. Encapsulation with sodium alginate plus gelatin

The experimental protocol A.1 was duplicated, substituting a mixture of 2% sodium alginate plus 5% gelatin for the 3.2% sodium alginate.

3. Encapsulation with carrageenan plus locust bean gum

The experimental protocol of A.1 was duplicated, using 0.25 to 0.8% carrageenan plus 0.4 to 1.0% locust bean gum instead of sodium alginate, and 50 to 500 millimolar ammonium chloride ($NH_4Cl$) instead of calcium chloride.

3.a As an alternative, 100 to 500 millimolar potassium chloride (KCl) can replace ammonium chloride.

4. Encapsulation with guar gum

The experimental protocol A.1 was duplicated, substituting 2% guar gum for sodium alginate and substituting 10 to 120 millimolar sodium tetraborate for calcium chloride.

EXAMPLE B (Celery somatic embryo)

Callus was induced from cotyledons and hypocotyls from two week old celery plants (*Apium graveolens* L., strains Utah Tall 5270, 5275, Calmario, and Golden Self Blanching) on SH medium containing 0.5 to 25 micromolar 2,4-D and 3 micromolar kinetin. Somatic embryos formed one to three months after transfer to SH medium containing 25 millimolar ammonium nitrate. The somatic embryos were then encapsulated as in protocol A.1. The encapsulated somatic embryos were germinated on SH medium (half strength) with 25 micromolar gibberellic acid (GA3) and 0.25 micromolar napthaleneacetic acid (NAA), and plants were produced.

EXAMPLE C (*Brassica oleracea* L.)

1. Organogenetic shoots

Cauliflower seeds (*Brassica oleracea* L. strain Monarch 73M) were germinated under sterile conditions on agar water. Eight days after germination, hypocotyl segments were placed on SH medium with 1 micromolar para-chlorophenoxyacetic acid (pCPA) and 10 micromolar kinetin to induce callus. After three to four weeks, the callus was transferred to SH medium with 10 micromolar indole acetic acid (IAA) and 3 micromolar kinetin and meristematic tissue formed. Some of the tissues formed adventitious shoots. The shoots were encapsulated as described in protocol A.1. and placed on SH medium with 20 millimolar ammonium nitrate and 3% w/v sucrose. The shoots emerged from the capsule and roots developed producing complete plants.

2. Somatic embryos

Somatic embryos with a distinct radicle and a distinct apical tip were produced from meristematic tissue from callus in the same manner as described for adventitious shoots in C.1. These embryos were encapsulated as in protocol A.1. and plants were produced.

EXAMPLE D (lettuce)

1. Organogenetic shoots

Seeds of lettuce (*Lactuca sativa* L. strain Arctic King) were germinated on agar water. Hypocotyl segments were placed on SH medium with 0.5 micromolar NAA, 2.5 micromolar kinetin, and 10 mm ammonium nitrate for the production of callus. After subculture, meristematic tissue was produced from the callus and adventitious shoots from part of the meristematic tissue. These shoots were encapsulated as in protocol A.1. When the capsules were placed on SH medium with 0.5 micromolar NAA and 2.5 micromolar kinetin the shoots emerged, roots formed, and complete plants were produced.

2. Lettuce somatic embryos

Somatic embryos with a distinct radicle and a distinct apical tip were produced from meristematic tissue from callus in the same manner as described for adventitious shoots in D.1. These embryos were encapsulated as in protocol A.1. and plants were produced.

EXAMPLE E (gopher plant organogenetic shoots)

Leaf mesophyll protoplasts were isolated from gopher plant, *Euphorbia lathyris* L. and callus produced according to techniques known to the art. Meristematic shoots were produced by placing the callus on Murashige and Skoog medium ("A Revised Medium for Rapid Growth and Bioassays with Tobacco Tissue Cultures." Physiol. Plant. 15: 473–97, 1962) containing in milligram per liter quantities: inositol (100), sodium phosphate (170), nicotinic acid (1), pyridoxine. HCl (1), thiamine.HCl (10) and sucrose (20,000) plus 0.4 nanomolar picloram and 20 micromolar 6-(gamma, gamma-dimethylallylamino)-purine.

The shoots were encapsulated as described in protocol A.1.

EXAMPLE F (wild mustard zygotic embryo)

Flower pods, two to four weeks after pollination, were removed from *Brassica campestris* L. plants growing in the wild. Zygotic embryos were dissected from the ovules contained within the flower pods and encapsulated as in protocol A.1. The embryos germinated when placed on an appropriate medium (see, M. Monnier, 1975, as cited elsewhere herein). Germination was inhibited for at least one month when embryos were encapsulated with 12% sucrose and placed on medium containing 12% (w/v)sucrose. Germination suppression was overcome by placing encapsulated embryos on medium containing 2% (w/v) sucrose and plants were obtained. Abscisic acid ($10^{-6}M$) was also used to suppress and control germination.

EXAMPLE G (*Brassica oleracea* L. zygotic embryo)

Zygotic embryos were excised from *Brassica oleracea* L. (variety PHW, Ccc-1) flowers and encapsulated as in protocol A.1. Plants were obtained on medium containing 2% (w/v) sucrose.

EXAMPLE H (hard outer covering)

1. *Brassica campestris* L. zygotic embryos were encapsulated as in protocol F. The capsules were allowed to dry down over a solution of sulfuric acid for one week. At that time alginate had dried around the embryo and had a breaking strength of greater than 60 kg/cm$^2$ (compared to a breaking strength of 7–15 Kg/cm$^2$ for newly encapsulated embryos). The dried capsules were placed on a medium with 2% w/v sucrose (see protocol F.), the embryos germinated, and plants were recovered.

2. Alfalfa somatic embryos were encapsulated as in protocol A.1. The capsules were coated with poly-L-amino acids for one hour to produce an outer covering with specific pore size. Polyamino acids used were poly-L-lysine (MW 4,000, 60,000, and 150,000) and poly-L-proline (MW 30,000) at 0.1% and 0.02% w/v for each molecular weight. The germination and embryo emergence frequency was 44%.

Although the foregoing invention has been described in some detail by way of illustration and example for purposes of clarity of understanding, it will be obvious to one skilled in the art that certain changes and modifications may be practiced within the scope of the appended claims.

I claim:

1. A process for creating an analog to natural botanic seed, which comprises:
    isolating meristematic tissue, which tissue has the potential to differentiate to produce an entire plant body and is free from botanical accessory structures; and
    encapsulating said isolated meristematic tissue in a hydrated gel capsule which will permit development of said plant body.

2. The process according to claim 1 wherein said meristematic tissue is somatic.

3. The process according to claim 2 wherein the somatic tissue is induced to form somatic embryos.

4. The process according to claim 3 wherein the tissue is isolated from a plant selected from the group consisting of *Medicago sativa* L., *Apium graveolens* L., *Brassica oleracea* L. and *Lactuca sativa* L..

5. The process according to claim 1 wherein said meristematic tissue is zygotic.

6. The process according to claim 1 wherein said meristematic tissue is germ line tissue.

7. The process according to claim 1 wherein said meristematic tissue is induced to form shoot meristem.

8. The process according to claim 1 wherein said gel comprises two or more distinct gel agents.

9. The process according to claim 1 wherein said gel comprises biologically active adjunctives in bio-affecting concentrations thereof.

10. The process according to claim 1 wherein the gel is selected from the group consisting of sodium alginate, guar gum, carrageenan with locust bean gum and sodium alginate with gelatin.

11. The process according to claim 1 further comprising treating said capsule to increase the breaking strength of its outer surface.

12. The process according to claim 1 further comprising treating said capsule to control the pore size of its outer surface.

13. An analog to natural botanic seed which comprises:
    meristematic tissue, having the potential to differentiate into an entire plant body, which tissue is encapsulated free from botanical accessory structures in a hydrated gel capsule which will permit development of said plant body.

14. The analog according to claim 13 wherein said meristematic tissue is tissue selected from the group consisting of somatic tissue, zygotic tissue and germline tissue.

15. The analog according to claim 13 wherein said gel comprises two or more distinct gel agents.

16. The analog according to claim 13 wherein said gel comprises biologically active adjunctives in bio-affecting concentrations thereof.

17. The analog according to claim 13 wherein said gel is selected from the group consisting of sodium alginate, guar gum, carrageenan with locust bean gum and sodium alginate with gelatin.

18. The analog according to claim 13 wherein the outer surface of said capsule has been treated to increase the breaking strength of its outer surface.

19. The analog according to claim 13 wherein the outer surface of said capsule has been treated to produce a desired pore size.

* * * * *